US010414871B2

(12) United States Patent
Knott et al.

(10) Patent No.: US 10,414,871 B2
(45) Date of Patent: Sep. 17, 2019

(54) MIXTURES OF CYCLIC BRANCHED SILOXANES OF THE D/T TYPE AND CONVERSION PRODUCTS THEREOF

(71) Applicant: Evonik Degussa GmbH, Essen (DE)

(72) Inventors: Wilfried Knott, Essen (DE); Horst Dudzik, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/719,775

(22) Filed: Sep. 29, 2017

(65) Prior Publication Data

US 2018/0134850 A1 May 17, 2018

(30) Foreign Application Priority Data

Nov. 15, 2016 (EP) .................................... 16198809
Feb. 16, 2017 (EP) .................................... 17156421

(51) Int. Cl.
| | | |
|---|---|---|
| C08G 77/06 | (2006.01) | |
| C07F 7/21 | (2006.01) | |
| C08G 77/04 | (2006.01) | |
| C08G 77/14 | (2006.01) | |
| C08G 77/10 | (2006.01) | |
| C08L 83/04 | (2006.01) | |
| C08G 77/12 | (2006.01) | |
| C08G 77/00 | (2006.01) | |

(52) U.S. Cl.
CPC .............. *C08G 77/06* (2013.01); *C07F 7/21* (2013.01); *C08G 77/045* (2013.01); *C08G 77/10* (2013.01); *C08G 77/14* (2013.01); *C08L 83/04* (2013.01); *C08G 77/12* (2013.01); *C08G 77/70* (2013.01)

(58) Field of Classification Search
None
See application file for complete search history.

(56) References Cited

U.S. PATENT DOCUMENTS

| | | |
|---|---|---|
| 2,758,124 A | 8/1956 | Schwenker |
| 4,631,208 A | 12/1986 | Westall |
| 5,093,101 A | 3/1992 | Knott et al. |
| 5,198,207 A | 3/1993 | Knott et al. |
| 5,221,499 A | 6/1993 | Klein et al. |
| 5,371,161 A | 12/1994 | Knott |
| 5,430,166 A | 7/1995 | Klein et al. |
| 5,430,167 A | 7/1995 | Klein et al. |
| 5,455,367 A | 10/1995 | Klein et al. |
| 5,475,127 A | 12/1995 | Klein et al. |
| 5,565,183 A | 10/1996 | Knott |
| 5,625,024 A | 4/1997 | Schlitte et al. |
| 5,670,129 A | 9/1997 | Klapdor et al. |
| 5,831,103 A | 11/1998 | Knott |
| 5,856,548 A | 1/1999 | Droese et al. |
| 5,934,579 A | 8/1999 | Hiersche et al. |
| 5,951,739 A | 9/1999 | Klapdor et al. |
| 5,972,285 A | 10/1999 | Knott |
| 5,981,812 A | 11/1999 | Eufinger et al. |
| 6,143,912 A | 11/2000 | Lindner et al. |
| 6,197,089 B1 | 3/2001 | Frommeyer et al. |
| 6,255,511 B1 | 7/2001 | Klein et al. |
| 6,291,622 B1 | 9/2001 | Droese et al. |
| 6,307,082 B1 | 10/2001 | Klein et al. |
| 6,387,154 B1 | 5/2002 | Frommeyer et al. |
| 6,444,007 B1 | 9/2002 | Knott et al. |
| 6,489,498 B2 | 12/2002 | Klein et al. |
| 6,521,771 B2 | 2/2003 | Frommeyer et al. |
| 6,659,162 B2 | 12/2003 | Frommeyer et al. |
| 6,730,749 B1 | 5/2004 | Burkhart et al. |
| 6,790,451 B2 | 9/2004 | Nakanishi |
| 6,854,506 B2 | 2/2005 | Knott et al. |
| 6,858,663 B2 | 2/2005 | Knott et al. |
| 6,874,562 B2 | 4/2005 | Knott et al. |
| 6,915,834 B2 | 7/2005 | Knott et al. |
| 6,942,716 B2 | 9/2005 | Knott et al. |
| 7,018,458 B2 | 3/2006 | Knott et al. |
| 7,125,585 B2 | 10/2006 | Dudzik et al. |
| 7,157,541 B2 | 1/2007 | Knott et al. |
| 7,196,153 B2 | 3/2007 | Burkhart et al. |
| 7,504,467 B2 | 3/2009 | Ochs |
| 7,598,334 B2 | 10/2009 | Ferenz et al. |
| 7,612,158 B2 | 11/2009 | Burkhart et al. |
| 7,612,159 B2 | 11/2009 | Burkhart et al. |
| 7,619,035 B2 | 11/2009 | Henning et al. |
| 7,645,848 B2 | 1/2010 | Knott et al. |
| 7,754,778 B2 | 7/2010 | Knott et al. |
| 7,825,205 B2 | 11/2010 | Knott et al. |
| 7,825,206 B2 | 11/2010 | Neumann et al. |
| 7,825,209 B2 | 11/2010 | Knott et al. |
| 8,138,294 B2 | 3/2012 | Henning et al. |
| 8,247,525 B2 | 8/2012 | Schubert et al. |
| 8,268,939 B2 | 9/2012 | Ebbrecht et al. |
| 8,283,422 B2 | 10/2012 | Schubert et al. |
| 8,309,664 B2 | 11/2012 | Knott et al. |
| 8,309,673 B2 | 11/2012 | Schubert et al. |
| 8,324,325 B2 | 12/2012 | Knott et al. |
| 8,334,355 B2 | 12/2012 | Henning et al. |
| 8,349,907 B2 | 1/2013 | Henning et al. |
| 8,420,748 B2 | 4/2013 | Henning et al. |
| 8,450,514 B2 | 5/2013 | Schubert et al. |

(Continued)

FOREIGN PATENT DOCUMENTS

| | | |
|---|---|---|
| CA | 2150841 | 4/1999 |
| CN | 102449032 | 5/2012 |

(Continued)

OTHER PUBLICATIONS

European Search Report dated Mar. 27, 2017 in EP 16 198 809 (7 pages).

(Continued)

*Primary Examiner* — Clinton A Brooks
(74) *Attorney, Agent, or Firm* — Philip P. McCann; Nexsen Pruet PLLC

(57) ABSTRACT

Mixtures of cyclic branched siloxanes having exclusively D and T units and having no functional groups, with the proviso that the cumulative proportion of the D and T units having Si-alkoxy and/or SiOH groups that are present in the siloxane matrix, determinable by $^{29}$Si NMR spectroscopy, is ≤2 mole percent, are described, as are branched organo-modified siloxanes obtainable therefrom.

11 Claims, No Drawings

(56) References Cited

U.S. PATENT DOCUMENTS

| | | |
|---|---|---|
| 8,455,603 B2 | 6/2013 | Ferenz et al. |
| 8,557,944 B2 | 10/2013 | Henning et al. |
| 8,598,295 B2 | 12/2013 | Henning et al. |
| 8,609,798 B2 | 12/2013 | Knott et al. |
| 8,623,984 B2 | 1/2014 | Henning et al. |
| 8,722,834 B2 | 5/2014 | Knott et al. |
| 8,722,836 B2 | 5/2014 | Knott et al. |
| 8,729,207 B2 | 5/2014 | Hartung et al. |
| 8,772,423 B2 | 7/2014 | De Gans et al. |
| 8,779,079 B2 | 7/2014 | Henning et al. |
| 8,802,744 B2 | 8/2014 | Knott et al. |
| 8,841,400 B2 | 9/2014 | Henning et al. |
| 8,921,437 B2 | 12/2014 | Knott et al. |
| 8,946,369 B2 | 2/2015 | Henning et al. |
| 8,957,009 B2 | 2/2015 | Schubert et al. |
| 8,969,502 B2 | 3/2015 | Knott et al. |
| 8,974,627 B2 | 3/2015 | Schubert et al. |
| 8,993,706 B2 | 3/2015 | Schubert et al. |
| 9,035,011 B2 | 5/2015 | Ferenz et al. |
| 9,068,044 B2 | 6/2015 | Schubert et al. |
| 9,315,614 B2 | 4/2016 | Schubert et al. |
| 9,334,354 B2 | 5/2016 | Ferenz et al. |
| 9,353,225 B2 | 5/2016 | Knott et al. |
| 9,441,145 B2 | 9/2016 | Schubert et al. |
| 9,481,695 B2 | 11/2016 | Knott et al. |
| 9,695,202 B2 | 7/2017 | Henning et al. |
| 2002/0161158 A1 | 10/2002 | Burkhart et al. |
| 2007/0128143 A1 | 6/2007 | Gruning et al. |
| 2009/0137752 A1 | 5/2009 | Knott et al. |
| 2010/0022435 A1 | 1/2010 | Henning et al. |
| 2010/0081781 A1 | 4/2010 | Schubert et al. |
| 2010/0239771 A1 | 9/2010 | Liu et al. |
| 2011/0076409 A1 | 3/2011 | Lenoble et al. |
| 2011/0230619 A1 | 9/2011 | Kuppert et al. |
| 2011/0301254 A1 | 12/2011 | Knott et al. |
| 2012/0046486 A1* | 2/2012 | Henning ............ C08G 77/08 556/451 |
| 2012/0068110 A1 | 3/2012 | Schubert et al. |
| 2012/0282210 A1 | 11/2012 | Henning et al. |
| 2013/0041115 A1 | 2/2013 | Knott et al. |
| 2013/0213267 A1 | 8/2013 | Fiedel et al. |
| 2013/0245304 A1 | 9/2013 | Schubert et al. |
| 2013/0345318 A1 | 12/2013 | Schubert et al. |
| 2014/0256844 A1 | 9/2014 | Henning et al. |
| 2014/0309446 A1 | 10/2014 | Amajjahe et al. |
| 2015/0004112 A1 | 1/2015 | Ritter et al. |
| 2015/0004113 A1 | 1/2015 | Ritter et al. |
| 2016/0053051 A1 | 2/2016 | Schubert et al. |
| 2016/0130290 A1 | 5/2016 | Knott et al. |
| 2016/0130402 A1 | 5/2016 | Schubert et al. |
| 2016/0160009 A1 | 6/2016 | Ferenz et al. |
| 2017/0081649 A1 | 3/2017 | Roseberg |
| 2017/0088667 A1 | 3/2017 | Fiedel et al. |
| 2017/0198099 A1 | 7/2017 | Knott |
| 2017/0226285 A1 | 8/2017 | Lobert et al. |

FOREIGN PATENT DOCUMENTS

| | | |
|---|---|---|
| DE | 1125180 B | 3/1962 |
| DE | 3716372 A1 | 11/1988 |
| DE | 102005004676 A1 | 8/2006 |
| DK | 2093244 T3 | 7/2015 |
| DK | 3050910 T3 | 2/2017 |
| EP | 0381318 A2 | 8/1990 |
| EP | 0514737 A1 | 11/1992 |
| EP | 0675151 A1 | 10/1995 |
| EP | 0685425 A1 | 12/1995 |
| EP | 0967236 A1 | 12/1999 |
| EP | 1350804 A1 | 10/2003 |
| EP | 1439200 A1 | 7/2004 |
| EP | 1717260 A1 | 11/2006 |
| EP | 2028214 A2 | 2/2009 |
| EP | 2918622 A1 | 9/2015 |
| EP | 3168273 A1 | 5/2017 |
| EP | 3168274 A1 | 5/2017 |
| WO | 02060621 A2 | 8/2002 |
| WO | 2009065644 A1 | 5/2009 |
| WO | 2010136279 A1 | 12/2010 |
| WO | 2013010747 A1 | 1/2013 |
| WO | 2016120023 A1 | 8/2016 |
| WO | 2017080747 A1 | 5/2017 |
| WO | 2017080749 A1 | 5/2017 |
| WO | 2017089068 A1 | 6/2017 |

OTHER PUBLICATIONS

European Search Report dated Mar. 30, 2017 in EP 17 156 421 (7 pages).

Lobert et al., U.S. Appl. No. 15/540,605, filed Jun. 29, 2017.

* cited by examiner

MIXTURES OF CYCLIC BRANCHED SILOXANES OF THE D/T TYPE AND CONVERSION PRODUCTS THEREOF

This application claims the benefit of European Application No. 16198809.2 filed on Nov. 15, 2016, and European Application No. 17156421.4 filed on Feb. 16, 2017, the disclosures of which are expressly incorporated herein by reference.

BACKGROUND

The invention relates to a process for preparing mixtures of cyclic branched siloxanes of the D/T type, to the mixtures of cyclic branched siloxanes of the D/T type themselves, and to the processing of these siloxanes to give functionalized branched siloxanes and/or branched siloxanes.

Cited as a reference in relation to the M, D, T, Q nomenclature used in the context of this document to describe the structural units of organopolysiloxanes is W. Noll, Chemie and Technologie der Silicone [Chemistry and Technology of the Silicones], Verlag Chemie GmbH, Weinheim (1960), page 2 ff.

In the preparation of organomodified siloxanes, especially branched function-bearing siloxanes, a difficulty frequently encountered is that competing processes that take place simultaneously in the reaction matrix can adversely affect the quality of the desired product.

Condensation and equilibration are among these competing processes, which have to be considered separately according to the synthetic problem. A great challenge is the homogeneous distribution of branching sites along a siloxane chain, corresponding to avoidance of T-structured domains. As can be inferred from the literature, the breakup of homologous siloxane chains consisting of T units under acid catalysis in particular is difficult and hence in effect cannot be accomplished in the presence of sensitive functional groups. With regard to the reactivity characteristics of M, D and T units, reference is made to M. A. Brook, "Silicon in Organic, Organometallic and Polymer Chemistry", John Wiley & Sons, Inc., New York (2000), p. 264 ff.

Especially in the preparation of branched siloxanes bearing reactive SiH groups, considerable efforts are therefore always made to reconcile the demand for uniform distribution of siloxane units as far as possible in a statistical manner with the demand for very substantial retention of the valuable silicon-bonded hydrogen.

Polyorganosiloxanes are prepared according to prior art by hydrolysis and condensation proceeding from methylchlorohydrosilanes having mixed substitution. Direct hydrolytic condensation of hydrogen-containing silanes, for example dimethylmonochlorosilane or methyldichlorosilane, is described, for example, in U.S. Pat. No. 2,758,124. In this case, the siloxane phase that separates in the hydrolysis is separated from the water phase having a hydrochloric acid content. Since this process is prone to gelation of the hydrosiloxanes, DE 11 25 180 describes an improved process utilizing an organic auxiliary phase, in which the hydrosiloxane formed is present as a separate phase dissolved in an organic solvent and, after separation from the acidic water phase and distillative removal of the solvent, is resistant to gelation. A further process improvement with regard to minimized solvent input is described by EP 0 967 236, the teaching of which involves first using only small amounts of water in the hydrolytic condensation of the organochlorosilanes, such that hydrogen chloride is driven out in gaseous form in the first step and can be sent directly to further end uses as a material of value.

Branched organomodified polysiloxanes can be described by a multitude of structures. In general, a distinction has to be made between a branch or crosslink which is introduced via the organic substituents and a branch or crosslink within the silicone chain. Organic crosslinkers for formation of siloxane skeletons bearing SiH groups are, for example, $\alpha,\omega$-unsaturated diolefins, divinyl compounds or diallyl compounds, as described, for example, in U.S. Pat. No. 6,730,749 or EP 0 381 318. This crosslinking by platinum-catalysed hydrosilylation downstream of the equilibration means an additional process step in which both intramolecular linkages and intermolecular linkages can take place. The product properties are additionally greatly affected by the different reactivities of the low molecular weight organic difunctional compounds that have a tendency to peroxide formation.

Multiple crosslinking of the silicone block of an organomodified polysiloxane with the organic block copolymer can be effected in various ways. EP 0 675 151 describes the preparation of a polyethersiloxane by hydrosilylation of a hydrosiloxane with a deficiency of hydroxy-functional allyl polyether, in which unconverted SiH functions are joined to the hydroxyl groups of the polyether substituents via an SiOC bond with addition of sodium methoxide. The increase in molar mass leads to broad scatter in the product properties, for example the viscosity. A similar approach to the formation of branched systems is described by U.S. Pat. No. 4,631,208, in which hydroxy-functional polyethersiloxanes are crosslinked by means of trialkoxysilanes. Both methods lead to intermolecular crosslinking of the polyethersiloxanes where it is not only difficult to control the increase in molar mass but where there are also associated unpredictable rises in viscosity. Following the aforementioned methods, what is obtained is not branching within the siloxane portion at constant molar mass, but crosslinking to give macromolecular multiblock copolymers.

Branching within the siloxane chain therefore already has to be effected in the course of production of the hydrosiloxane, in order to get round the described disadvantages of the crosslinking. Branches within the siloxane chain require the synthetic incorporation of trifunctional silanes, for example trichlorosilanes or trialkoxysilanes.

As known to the person skilled in the art, the rate of hydrolysis of the organochlorosilanes rises in the following series (C. Eaborn, Organosilicon Compounds, Butterworths Scientific Publications, London 1960, p. 179): $SiCl_4 > RSiCl_3 \gg R_2SiCl_2 > R_3SiCl$.

Therefore, in the hydrolysis and condensation reactions of trichlorosilanes, there is an elevated tendency to formation of highly crosslinked gels compared to the slower hydrolysis and condensation reactions of difunctional and monofunctional organochlorosilanes. The established processes for hydrolysis and condensation of dichloro- and monochlorosilanes are therefore not directly applicable to trichlorosilanes; instead, it is necessary to take indirect routes via multistage processes.

Building on this finding, it is also necessary to conduct the preparation of singly branched hydrosiloxanes by incorporation of not more than one trifunctional monomer per siloxane chain in a two-stage process according to the prior art. In a first step, a trifunctional low molecular weight hydrosiloxane is prepared by hydrolysis and condensation from 1,1,3,3-tetramethyldisiloxane and methyltriethoxysilane, as taught, for example, by DE 37 16 372. Only in a second step is equilibration then possible with cyclic siloxanes to give higher molar masses, as explained by DE 10 2005 004676. For further conversion—and therefore only in a third step—the singly branched hydrosiloxane thus prepared can be provided by the methods known per se for functionalization of siloxane compounds having SiH groups with organic substituents.

For synthesis of multiply branched hydrosiloxanes which, by definition, have more than one trifunctional monomer per siloxane chain, there are likewise two-stage syntheses in the prior art. In principle, it is possible to proceed from hydrosiloxanes and to subject the SiH functions, with addition of water and precious metal catalyst, to dehydrogenative conversion to silanols which are then condensed in turn with hydrosiloxanes. This procedure is described in U.S. Pat. No. 6,790,451 and in EP 1 717 260. Quite apart from the costs of the precious metal catalysis, the poor storage stability of the silanols, which have a tendency to autocondensation, makes it difficult to accomplish a reproducible, controlled process regime.

A further option described in U.S. Pat. No. 6,790,451 is that of preparing a copolymer from trichloromethylsilane or trialkoxymethylsilane with hexamethyldisiloxane or trimethylchlorosilane, also called MT polymer therein, which is equilibrated in a second step together with a polydimethyl (methylhydro)siloxane copolymer. The preparation of such MT polymers entails the use of strong bases or strong acids, in some cases in combination with high reaction temperatures, and results in prepolymers of such high viscosity that the neutralization thereof is made considerably more difficult and hence further processing to give end products of constant composition and quality is significantly limited.

According to EP 0 675 151, first of all, the hydrolysis and condensation of the SiH-free branched silicone polymer is conducted in xylene in such a way that the final occlusion of the precondensate is conducted with a large excess of hexamethyldisiloxane and, in the second step, the equilibration is undertaken with methylhydropolysiloxane to give a branched hydrosiloxane (preparation method 6, ibid.). As an alternative, the teaching of EP 0 675 151 relates to a procedure for preparation of non-SiH-functional branched siloxanes including merely a partial condensation of the methyltrichlorosilane used (preparation method 7, ibid.). However, these two strategies do not address the need for a universally utilizable preparation method for branched siloxanes.

WO2009065644 (A1) teaches a process for preparing branched SiH-functional siloxanes by reacting a mixture comprising a) one or more SiH-functional siloxanes, b) one or more SiH function-free siloxanes and c) one or more trialkoxysilanes with addition of water and in the presence of at least one Brønsted-acidic catalyst, wherein the reaction is conducted in one process step. The technical limits of this process become clear from the disclosure therein with regard to the conservation of the SiH functionality introduced into the system. This shows the need to work with at least two acidic catalysts (trifluoromethanesulfonic acid vs. trifluoromethanesulfonic acid and sulfuric acid ion exchange resin, ibid. examples 5 and 6) for sensitive SiH-functional branched siloxane structures, which makes the process extremely inconvenient and costly in terms of its industrial implementation.

There has already been speculation in the literature about the possible existence of siloxanes formed exclusively from D and T units. As stated by W. Noll in Chemie and Technologie der Silicone, Weinheim (1960), pages 181-182, D. W. Scott (J. Am. Chem. Soc. 68, 356, 1946) was the first to suggest that bicyclic compounds of siloxanes having D and T units derive from an extremely dilute co-hydrolysis of dimethyldichlorosilane and methyltrichlorosilane with subsequent thermal rearrangement. It was possible to isolate isomers in amounts of not even 1% from the viscous co-hydrolysate at bottom temperatures between 350 and 600° C., and they were then described by cryoscopic and elemental analysis with very high levels of uncertainty. Scott speculates that his compounds having D-T structures contain T structural elements joined directly to one another and not via D units. The interpretation of the results in Scott is based on the premise that all the SiC bonds present in the co-hydrolysate withstand the severe thermal treatment that he chose.

Makarova et al. (Polyhedron Vol. 2, No. 4, 257-260 (1983)) prepared 10 oligomeric methylsiloxanes having cyclic and linear segments by the controlled low-temperature condensation of siloxanes having SiOH groups and containing SiCl groups in the presence of organic amines such as triethylamine or aniline in benzene or diethyl ether as solvents, separated off the precipitated amine hydrochlorides, and washed and then fractionally distilled the crude reaction products. Subsequently, the bicyclic methylsiloxanes were subjected to pyrolysis at temperatures between 400 and 600° C., and the pyrolysis products were characterized by gas chromatography. The low molecular weight compounds used in the course of this study, for example hydroxynonamethylcyclopentasiloxane, hydroxyheptamethylcyclotetrasiloxane, dihydroxytetramethyldisiloxane, from the point of view of the silicone chemistry conducted on the industrial scale, are considered to be exotic species of purely academic interest.

More particularly, the pure-chain siloxane compounds of the D/T type defined in terms of molar mass that have been synthesized by this route are unsuitable for the production of organomodified siloxanes that are employed in demanding industrial applications, for example in PU foam stabilization or in the defoaming of plastics, etc. Active ingredients that effectively address such a field of use are always characterized by a broad oligomer distribution comprising high, moderate and low molar masses, since the oligomers present therein, depending on their molar mass and hence their diffusion characteristics, are very commonly imputed to have differentiated surfactant tasks in different time windows of the respective process. Specifically in the case of the branched organomodified siloxanes, due to the reaction characteristics of M, D and T units that have been discussed at the outset, however, a good oligomer distribution combined with a uniform distribution of siloxane units in a statistical manner as far as possible in the individual molecules can only be achieved when the starting material of the D/T type used already itself conforms to a distribution function. This is all the more true when the organomodification is effected via an intermediate bearing SiH groups.

Acknowledging this prior art, there is no apparent real solution for preparation of branched organomodified siloxanes.

SUMMARY

It has now been found that, astonishingly, the problem outlined can be solved by conducting the preparation process for obtaining branched organomodified siloxanes in such a way that in a first step the preparation of mixtures of cyclic branched siloxanes having exclusively D and T units and having essentially no functional groups is conducted, where a trialkoxysilane in a solvent is reacted with siloxane cycles and/or, preferably or, α,ω-dihydroxypolydimethylsiloxane with addition of water and in the presence of at least one acidic catalyst, especially with the proviso that the cumulative proportion of the D and T units, the Si-alkoxy and SiOH groups respectively, present in the siloxane matrix, determinable by $^{29}$Si NMR spectroscopy, is not more than 2 mole percent, and in a second step the cyclic branched siloxanes are subjected to acidic equilibration with silanes and/or siloxanes, especially with functional silanes and/or siloxanes.

This gives rise to the following items of subject-matter of the invention.

DETAILED DESCRIPTION

The invention provides mixtures of cyclic branched siloxanes having exclusively D and T units and having no functional groups, with the proviso that the cumulative proportion of the D and T units having Si-alkoxy and/or SiOH groups that are present in the siloxane matrix, determinable by $^{29}$Si NMR spectroscopy, is ≤2 mole percent, otherwise having no functional groups.

The invention further provides processes for preparing mixtures of cyclic branched siloxanes having exclusively D and T units and having essentially no functional groups, especially mixtures of cyclic branched siloxanes having exclusively D and T units, with the proviso that the cumulative proportion of the D and T units having Si-alkoxy and/or SiOH groups present in the siloxane matrix, determinable by $^{29}$Si NMR spectroscopy, is ≤2 mole percent, otherwise having no functional groups, wherein a trialkoxysilane in a solvent is reacted with siloxane cycles and/or, preferably or, α,ω-dihydroxypolydimethylsiloxane, with addition of water and in the presence of at least one acidic catalyst.

The invention still further provides a process for preparing branched organomodified siloxanes, wherein a first step cyclic branched siloxanes are provided, preferably mixtures of cyclic branched siloxanes having exclusively D and T units and having no functional groups, with the proviso that the cumulative proportion of the D and T units having Si-alkoxy and/or SiOH groups that are present in the siloxane matrix, determinable by $^{29}$Si NMR spectroscopy, is ≤2 mole percent, otherwise having no functional groups, in a second step the cyclic branched siloxanes are equilibrated under acidic conditions with silanes and/or siloxanes.

The invention and its subject matter are more particularly elucidated hereinafter.

In the inventive mixtures of cyclic branched siloxanes having exclusively D and T units, in a preferred embodiment of the invention, the ratio of D to T units is between 10:1 and 3:1, preferably between 6:1 and 4:1.

In a further preferred embodiment of the invention, the molar mass ratio $M_w/M_n$ of the mixture is in the range of $2<M_w/M_n<50$. These parameters can be determined from toluenic solutions of the siloxanes by gel permeation chromatography (GPC), which, with utilization of a refractive index detector, by comparison with a polystyrene standard, permits the determination of the mean molar mass $M_w$ thereof and the molar mass distribution $M_w/M_n$ thereof.

When the mixtures of cyclic branched siloxanes having exclusively D and T units, as described above, have the feature that the branching T unit derives from alkyltrialkoxysilanes and/or, preferably or, phenyltrialkoxysilanes, this is a further preferred embodiment of the invention.

A preferred embodiment of the invention is likewise when the branching T unit derives from methyltriethoxysilane.

The aforementioned mixtures according to the invention can especially be obtained via the process according to the invention for preparing mixtures of cyclic branched siloxanes having exclusively D and T units, by reacting a trialkoxysilane in a solvent with siloxane cycles and/or, preferably or, α,ω-dihydroxypolydimethylsiloxane, with addition of water and in the presence of at least one acidic catalyst. This comprises hydrolysis and condensation under acid-equilibrating conditions.

There follows a more particular description of a procedure which is preferred but nevertheless is merely an example and therefore does not restrict the subject-matter of the invention:

Preferably, trialkoxysilane and siloxane cycles can be initially charged in a suitable solvent (for example toluene or cyclohexane), and a catalytic amount of an equilibrating acid (e.g. 0.2 m % of trifluoromethanesulfonic acid, based on the mass of the reactants without solvent) can be added.

Preliminary equilibration is effected, for example, in toluenic phase at 60° C. for 4 hours, then a water/ethanol mixture (100% excess of $H_2O$ based on the groups to be condensed) is added and the reaction mixture is heated, for example to reflux temperature (about 80° C.) for 4 hours. The reflux condenser is preferably replaced by a water separator and the reaction mixture is heated to about 100° C. within one hour, in the course of which the bottom temperature rises constantly with progressive discharge of the volatiles. When the excess water has been separated out completely, the reaction mixture becomes clear.

After cooling to about 70° C., for example, a second portion of a water/ethanol mixture (about ⅓ of the amount used in the preliminary equilibration step) is added and the reaction mixture is heated to reflux temperature (about 80° C.) for 1 hour. The reflux condenser is replaced by a water separator and the reaction mixture is heated to about 100° C. The bottom temperature rises with progressive discharge of the volatiles. At the juncture when the excess water has been separated out completely, the reaction mixture becomes clear.

The reaction mixture is cooled to about 60° C. and, for the purpose of neutralization, 4 m % of $NaHCO_3$ is added while stirring. After about 30 minutes, the reaction mixture is freed of the solids by filtration. The solvent (toluene) is distilled off at 70° C. and an applied auxiliary vacuum of 1 mbar.

What are obtained are clear colorless liquids of low viscosity, the corresponding $^{29}$Si NMR spectrum of which demonstrates the dominating presence of D and T units. The ratio of D to T units is preferably between 10:1 and 3:1, preferably between 6:1 and 4:1. By spectroscopy, Si-alkoxy and SiOH groups are found with signal intensities of about 0.5% to 1% at most, if at all. The determinable cumulative proportion of the D and T units having Si-alkoxy and SiOH groups present in the siloxane matrix is in any case ≤2 mole percent.

The aforementioned illustrative procedure leads to excellent results with a view to the aim to be achieved in accordance with the invention.

If, in the process according to the invention, the solvent used is an inert water-immiscible silicon-free solvent, preferably from the group comprising the isomeric xylenes, alkylaromatics such as preferably toluene and/or cycloaliphatics such as preferably cyclohexane, or else ethyl carbonate, advantageously in mass ratios of solvent to the siloxane of 1:1 to 5:1, this is a preferred embodiment of the invention.

Depending on the desired D/T ratio, the amount of solvent is preferably such as to assure viscosities that can be handled in an efficient manner over the course of the reaction. Preferably, mass ratios of solvent to the siloxane of 1:1 to 5:1 are chosen. Particularly in the case of D/T ratios less than 5:1, an unadjusted amount of solvent can lead to rises in viscosity extending as far as gelation. On the other hand, a few preliminary tests (see Example 4 (gelated system) and Example 5 (manageable system)), once the solvent has been chosen, can be used to fix the optimal mass ratio of solvent to the siloxane.

The acidic catalyst used in the process according to the invention, in a preferred embodiment of the invention, may be
  (a) para-toluenesulfonic acid, trifluoromethanesulfonic acid, trichloroacetic acid, sulfuric acid, perchloric acid, phosphoric acid and/or hexafluorophosphoric acid, preferably in amounts of 0.1 to 2.0 percent by weight, more preferably in amounts of 0.15 to 1.0 percent by weight, based in each case on the silicon-containing component of the reaction matrix,
or
  (b) a macrocrosslinked ion exchange resin containing sulfonic acid groups, preferably in amounts of 1.0 to 10.0 percent by weight, more preferably in amounts of 2.0 to 6.0 percent by weight, based in each case on the silicon-containing component of the reaction matrix.

Suitable acidic catalysts are described in more detail hereinafter.

If the reaction is conducted at temperatures in the range from 10° C. to 150° C., preferably 20° C. to 120° C., especially for 40° C. to 110° C., this is a further preferred embodiment of the invention.

If an at least 100% $H_2O$ excess based on the groups to be condensed is used, this is likewise a further preferred embodiment of the invention.

If the reaction comprises a preliminary equilibration step at temperatures of T>40° C., followed by a condensation initiated by addition of water at temperatures of T>60° C., where the water is added in one portion, in several portions or continuously, this is again a further-preferred embodiment of the invention.

As already set out in detail further up, the invention further provides a process for preparing branched organomodified siloxanes, wherein, in a first step, cyclic branched siloxanes are provided, preferably mixtures of cyclic branched siloxanes having exclusively D and T units and having no functional groups, with the proviso that the cumulative proportion of the D and T units having Si-alkoxy and/or SiOH groups that are present in the siloxane matrix, determinable by $^{29}Si$ NMR spectroscopy, is not more than 2 mole percent, otherwise having no functional groups, and in a second step the cyclic branched siloxanes are subjected to acidic equilibration with silanes and/or siloxanes, preferably functional silane and/or siloxane.

Functional silane and/or siloxane are understood to mean all those compounds comprising one silicon atom and/or multiple silicon atoms which can be incorporated into the copolymer (corresponding to cyclic branched siloxanes) by way of acidic equilibration. More particularly, these acid-equilibratable silanes or siloxanes, as well as any hydrogen, alkyl or aryl, or vinyl substituents present, also have hydroxyl, alkoxy and chlorine substituents. Likewise suitable here are functional silanes or siloxanes that bear acidic moieties such as toluenesulfonate, trifluoromethylsulfonate and sulfate radicals.

As a special case, branched silicone oils are obtainable by the acidic co-equilibration of the cyclic branched siloxane of the D/T type obtained in the first step with hexamethyldisiloxane and/or, preferably or, polydimethylsiloxanes. A corresponding process according to the invention for preparing branched silicone oils, wherein in a first step mixtures of cyclic branched siloxanes are provided, as described above, and in a second step the mixtures of cyclic branched siloxanes are reacted with polydimethylsiloxanes or hexamethyldisiloxane, thus corresponds to a further part of the subject-matter of the invention.

However, it is more preferable in accordance with the invention to provide branched organomodified siloxanes. For achievement of such a final organomodified siloxane structure, an acidic equilibration with functional silanes and/or siloxanes is conducted as the second step.

Suitable acidic catalysts for both steps of the process according to the invention are the strong acids (equilibrating acids) known from the prior art for siloxanes, i.e. mineral acids, for example sulfuric acid, but also sulfonic acids, fluoroalkylsulfonic acids, for example trifluoromethanesulfonic acid, acidic aluminas or acidic ion exchange resins, for example the products known by the Amberlite®, Amberlyst® or Dowex® and Lewatit® brand names.

In the process according to the invention, it is possible to use either natural ion exchangers, for example zeolites, montmorillonites, attapulgites, bentonites and other aluminosilicates, or synthetic ion exchangers. The latter are preferably solids (usually in granular form) with a three-dimensional, water-insoluble, high molecular weight matrix based on phenol-formaldehyde resins or copolymers of styrene-divinylbenzene into which numerous "anchor groups" of different acidity have been incorporated.

Acidic ion exchangers used advantageously in the context of the present invention include those as described in EP 1 439 200.

Preference is given to using sulfonic acid catalysts and very particular preference to using trifluoromethanesulfonic acid.

In the first step of the process according to the invention (corresponding to the preparation of the mixtures of cyclic branched siloxanes as described above), it is possible in principle to use any trialkoxysilanes. Trialkoxysilanes used may be those in which the alkoxy radicals are all the same or all different or in which some are the same. Trialkoxysilanes used may especially be triethoxysilanes, preferably methyltriethoxysilane, alkyltriethoxysilanes, for example n-propyltriethoxysilane, isobutyltriethoxysilane, pentyltriethoxysilane, hexyltriethoxysilane, octyltriethoxysilane, hexadecyltriethoxysilane, n-octadecyltriethoxysilane, halogenated or pseudohalogenated alkyltrialkoxysilanes, especially alkyltriethoxysilanes, for example chloropropyltriethoxysilane, tridecafluoro-1,1,2,2-tetrahydrooctyltriethoxysilane, nonafluoro-1,1,2,2-tetrahydrohexyltriethoxysilane, 3-cyanopropyltriethoxysilane, trialkoxysilanes, especially triethoxysilanes having functional groups, for example 3-methacryloyloxypropyltriethoxysilane, 3-mercaptopropyltriethoxysilane, 5-(bicycloheptenyl)triethoxysilane, phenyltriethoxysilane, (p-chloromethyl)phenyltriethoxysilane, N-(3-triethoxysilylpropyl)-4,5-dihydroimidazole or dihydro-3-[3-(triethoxysilyl)propyl]furan-2,5-dione. It may be advantageous for organically functionalized trialkoxysilanes to be used as branching unit (included in the equilibration).

Suitable compounds for functionalization of these cyclic branched siloxanes, as described in detail further up, in the second step are in principle all acid-equilibratable silicon compounds, preferably silanes and/or siloxanes, which can be used for acidic equilibration.

The silanes and/or siloxanes used are any acid-equilibratable silicon compounds, the silanes used especially being diethoxydimethylsilane, trimethylalkoxysilane and dimethyldichlorosilane, and the siloxanes used especially being tetramethyldisiloxane, α,ω-dihydropolydimethylsiloxanes, poly(methylhydro)siloxanes, α,ω-dialkoxypolydimethylsiloxanes or α,ω-divinylpolydimethylsiloxanes.

A crucial advantage of the preparation process according to the invention is that the synthesis of mixtures of cyclic branched siloxanes without functional groups, which is the aim in the first step, can be conducted under severe reaction conditions, for example at a high acid concentration and high temperatures, without product damage since there are no sensitive moieties present at all (for example SiH functions). Optimal incorporation of branching units (T structures) into the molecular skeletons of the siloxane oligomers is thus possible, where the T structures are ideally separated by D units in each case and are not present in cumulated form in a domain-like manner, as shown by the $^{29}$Si NMR spectroscopy, especially in the shift region of the T structures.

Gas chromatography analysis shows that, typically, simple siloxane cycles such as $D_4$ (octamethylcyclotetrasiloxane), $D_5$ (decamethylcyclopentasiloxane) and $D_6$ (dodecamethylcyclohexasiloxane) are present in the equilibrates only in proportions by weight of less than 10%.

If desired for the respective later application (for example within the scope of the VOC discussion (VOC=volatile organic compounds) or of anti-fogging), these siloxane cycles can be removed by simple distillation and recycled.

On the other hand, the thermal reaction conditions chosen in the context of the inventive process can be called extremely moderate, compared to the temperatures of up to 600° C. described in the literature.

The cyclic branched siloxanes of the D/T type are obtained in virtually quantitative yields, based in each case on trialkoxysilane used.

It will be immediately apparent to the person skilled in the art that the branched organomodified siloxanes obtained by acidic equilibration from the second step are suitable as starting material for production of stabilizers for PUR foams, for production of defoamers, for production of paint additives, for production of emulsifiers, especially of cosmetic emulsifiers, for production of cosmetic conditioners, for production of deaerating agents, for production of demulsifiers, for production of textile finishes, for production of building protection additives, for production of polymer additives, especially anti-scratch additives, for production of antifouling additives or coatings, and for production of anti-icing coatings. This use forms a further part of the subject-matter of the present invention.

Depending on the functionality incorporated in the second step (e.g. SiH group (see Example 6) or SiCl group (see Example 10)), for all these aforementioned applications, after selection of appropriate co-reactants, SiC-bonded final products are obtainable via hydrosilylation, or else SiOC-bonded final products are obtainable via dehydrogenative SiOC bond formation or condensation by the known methods of silicon chemistry.

The $^{29}$Si NMR samples, in the context of this invention, are analysed at a measurement frequency of 79.49 MHz in a Bruker Avance III spectrometer equipped with a 287430 sample head with gap width 10 mm, dissolved at 22° C. in CDCl$_3$ and against tetramethylsilane (TMS) as external standard [δ($^{29}$Si)=0.0 ppm].

The weight-average molar mass $M_w$ and the molar mass distribution $M_w/M_n$ are determined in the context of this invention using an EcoSEC GPC/SEC instrument from TOSOH Bioscience GmbH by gel permeation chromatography from toluenic solutions of the siloxanes. A Micro SDV 1000/10000 column of length 55.00 cm is used, combined with an EcoSEC RI detector (dual flow refractive index detection). The polystyrene standard covers the molar mass range from 162 g/mol to 2 520 000 g/mol.

EXAMPLES

1) Preparation of a Cyclic Branched Siloxane Having a Target D/T Ratio of 8:1 (Inventive)

In a 500 ml four-neck round-bottom flask with a precision glass stirrer and a reflux condenser on top, 40.5 g (0.227 mol) of methyltriethoxysilane are heated to 60° C. together with 134.5 g (0.363 mol) of decamethylcyclopentasiloxane in 200 ml of toluene while stirring, 0.375 g of trifluoromethanesulfonic acid is added and the mixture is equilibrated for 4 hours. Then 12.3 g of water and 3.1 g of ethanol are added and the mixture is heated to reflux temperature at about 80° C. for a further 4 hours. The reflux condenser is exchanged for a distillation system, and the constituents that are volatile up to 100° C. are distilled off within the next hour. Then the distillation system is replaced by the reflux condenser, 6.15 g of water and 1.5 g of ethanol are added to the mixture and the mixture is left to boil for a further hour. The reflux condenser is then replaced once again by a distillation system, and the constituents that are volatile up to 100° C. are removed over the course of the next hour. The mixture is cooled to 60° C. and then 4 m % of sodium hydrogencarbonate is added, the mixture is stirred for half an hour, then the salt is separated from the liquid phase with the aid of a fluted filter. The volatiles are distilled off at 70° C. and a pressure of <1 mbar on a rotary evaporator, and a colorless mobile liquid is isolated, the $^{29}$Si NMR spectrum of which indicates a D/T ratio of 7.62:1 (target: 8:1).

The GPC has a broad molar mass distribution, characterized by $M_w$=70317 g/mol; $M_n$: 1941 g/mol and $M_w/M_n$=36.24.

2) Preparation of a Cyclic Branched Siloxane Having a Target D/T Ratio of 6:1 (Inventive)

Analogously to Example 1, in a 500 ml four-neck round-bottom flask with a precision glass stirrer and a reflux condenser on top, 52.2 g (0.293 mol) of methyltriethoxysilane are heated to 60° C. together with 130.3 g (0.351 mol) of decamethylcyclopentasiloxane in 200 ml of toluene while stirring, 0.400 g of trifluoromethanesulfonic acid is added and the mixture is equilibrated for 4 hours. Then 15.8 g of water and 4.0 g of ethanol are added and the mixture is heated to reflux temperature at about 80° C. for a further 4 hours. The reflux condenser is exchanged for a distillation system, and the constituents that are volatile up to 100° C. are distilled off within the next hour. Then the distillation system is replaced by a reflux condenser, 7.90 g of water and 2.0 g of ethanol are added to the mixture and the mixture is left to boil for a further hour. The reflux condenser is then replaced once again by a distillation system, and the constituents that are volatile up to 100° C. are removed over the course of the next hour. The mixture is cooled to 60° C. and then 4 m % of sodium hydrogencarbonate is added, the mixture is stirred for half an hour, then the salt is separated from the liquid phase with the aid of a fluted filter. The volatiles are distilled off at 70° C. and a pressure of <1 mbar on a rotary evaporator, and a colorless mobile liquid is isolated, the $^{29}$Si NMR spectrum of which indicates a D/T ratio of 5.85:1 (target: 6:1).

3) Preparation of a Greater Amount of a Cyclic Branched Siloxane Having a Target D/T Ratio of 6:1 (Inventive)

In a 4000 ml four-neck round-bottom flask with a precision glass stirrer and a reflux condenser on top, 261.0 g (1.46 mol) of methyltriethoxysilane are heated to 60° C. together with 652.5 g (1.76 mol) of decamethylcyclopentasiloxane and 200 ml of toluene while stirring, 1.983 g of trifluoromethanesulfonic acid is added and the mixture is equilibrated for 4 hours. Then 79.0 g of water and 19.75 g of ethanol are added and the mixture is heated to reflux temperature at about 80° C. for a further 4 hours. The reflux condenser is exchanged for a distillation system, and the constituents that are volatile up to 100° C. are distilled off within the next hour. Then the distillation system is replaced by a reflux condenser, 26.30 g of water and 6.6 g of ethanol are added to the mixture and the mixture is left to boil for a further hour. The reflux condenser is then replaced once again by a distillation system, and the constituents that are volatile up to 100° C. are removed over the course of the next hour. The mixture is cooled to 60° C. and then 4 m % of sodium hydrogencarbonate is added, the mixture is stirred for half an hour, then the salt is separated from the liquid phase with the aid of a fluted filter. The volatiles are distilled off at 70° C. and a pressure of <1 mbar on a rotary evaporator, and a colorless mobile liquid is isolated, the corresponding $^{29}$Si NMR spectrum of which indicates a D/T ratio of 5.74:1 (target: 6:1). The dynamic viscosity is 598 mPas at 25° C. The GC shows residual contents of $D_4$=3.2%, $D_5$=3.9% and $D_6$=1.4%.

The GPC has a broad molar mass distribution, characterized by $M_w$=91965 g/mol; $M_n$: 2214 g/mol and $M_w/M_n$=41.54.

4) Preparation of a Cyclic Branched Siloxane Having a Target D/T Ratio of 4:1 (Unadjusted Amount of Solvent)

Analogously to Example 1, in a 500 ml four-neck round-bottom flask with a precision glass stirrer and a reflux condenser on top, 73.5 g (0.412 mol) of methyltriethoxysilane are heated to 60° C. together with 122.3 g (0.33 mol) of decamethylcyclopentasiloxane in 220 ml of toluene while stirring, 0.436 g of trifluoromethanesulfonic acid is added and the mixture is equilibrated for 4 hours. Then 22.3 g of water and 5.6 g of ethanol are added and the mixture is heated to reflux temperature at about 80° C. for a further 4 hours. The reflux condenser is exchanged for a distillation system, and the constituents that are volatile up to 100° C. are distilled off within the next hour. Then the distillation system is replaced by a reflux condenser, 7.50 g of water and 1.9 g of ethanol are added to the mixture and the mixture is left to boil for a further hour. The reflux condenser is then replaced once again by a distillation system. In the course of the subsequent distillation, the viscosity of the bottoms rises so significantly that the mass of silicone gelates and is discarded.

5) Preparation of a Cyclic Branched Siloxane Having a Target D/T Ratio of 4:1 (Inventive, Adjusted Amount of Solvent of 1:3)

Analogously to Example 1, in a 500 ml four-neck round-bottom flask with a precision glass stirrer and a reflux condenser on top, 36.8 g (0.206 mol) of methyltriethoxysilane are heated to 60° C. together with 61.2 g (0.165 mol) of decamethylcyclopentasiloxane in 330 ml of toluene while stirring, 0.218 g of trifluoromethanesulfonic acid is added and the mixture is equilibrated for 4 hours. Then 11.2 g of water and 2.8 g of ethanol are added and the mixture is heated to reflux temperature at about 80° C. for a further 4 hours. The reflux condenser is exchanged for a distillation system, and the constituents that are volatile up to 100° C. are distilled off within the next hour. Then the distillation system is replaced by a reflux condenser, 2.70 g of water and 0.9 g of ethanol are added to the mixture and the mixture is left to boil for a further hour. The reflux condenser is then replaced once again by a distillation system, and the constituents that are volatile up to 100° C. are removed over the course of the next hour. The mixture is cooled to 60° C. and then 4 m % of sodium hydrogencarbonate is added, the mixture is stirred for half an hour, then the salt is separated from the liquid phase with the aid of a fluted filter. The volatiles are distilled off at 70° C. and a pressure of <1 mbar on a rotary evaporator, and a colorless mobile liquid is isolated, the $^{29}$Si NMR spectrum of which indicates a D/T ratio of 3.6:1 (target: 4:1).

The GPC has a molar mass distribution characterized by $M_w$=12344 g/mol; $M_n$:3245 g/mol and $M_w/M_n$=2.63.

6) Preparation of a Branched Hydrosiloxane Having Terminal SiH Functions from the Cyclic Branched Siloxane Prepared in Example 1 with α,ω-dihydropolydimethylsiloxane and decamethylcyclopentasiloxane 37.4 g of the cyclic branched siloxane prepared in Example 1 are heated to 40° C. together with 6.3 g of an α,ω-dihydropolydimethylsiloxane (SiH value: 2.90 eq/kg) and 186.3 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top for 6 hours, then 5 g of sodium hydrogencarbonate were added and the mixture was stirred for a further 30 minutes. With the aid of a filter press (Seitz K 300 filter disc), the salt was separated from the equilibrate.

What is obtained is a colorless branched hydrosiloxane having dimethylhydrosiloxy functions in its termini (SiH value: 0.30 eq/kg). The corresponding $^{29}$Si NMR spectrum confirms the target structure.

7) Preparation of a Branched Siloxane Having Terminal Ethoxy Functions (Inventive)

114.8 g of the cyclic branched siloxane prepared in Example 2 are heated to 60° C. together with 33.9 g of dimethyldiethoxysilane and 101.1 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top for 6 hours, then 5 g of sodium hydrogencarbonate were added and the mixture was stirred for a further 30 minutes. With the aid of a filter press (Seitz K 300 filter disc), the salt was separated from the equilibrate.

The corresponding $^{29}$Si NMR spectrum confirms the target structure.

8) Preparation of a Branched Siloxane Having Terminal Vinyl Functions (Inventive)

109.2 g of the cyclic branched siloxane prepared in Example 3 are heated to 60° C. together with 41.3 g of divinyltetramethyldisiloxane and 99.5 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top for 6 hours, then 5 g of sodium hydrogencarbonate were added and the mixture was stirred for a further 30 minutes. With the aid of a filter press (Seitz K 300 filter disc), the salt was separated from the equilibrate.

The corresponding $^{29}$Si NMR spectrum confirms, as the target structure, a branched siloxane bearing terminal vinyl functions.

9) Preparation of a Branched Silicone Oil (Inventive)

111.6 g of the cyclic branched siloxane prepared in Example 3 are heated to 60° C. together with 36.7 g of hexamethyldisiloxane and 101.7 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top for 6 hours, then 5 g of sodium hydrogencarbonate were added and the mixture was stirred for a further 30 minutes. With the aid of a filter press (Seitz K 300 filter disc), the salt was separated from the equilibrate.

The corresponding $^{29}$Si NMR spectrum confirms, as the target structure, a branched non-functional silicone oil.

10) Preparation of a Branched Sulfato-Bridged Siloxane Having Terminal Chlorine Functions (Chlorosiloxanyl Sulfate, Inventive)

a) Preparation of a Linear Chlorosiloxanyl Sulfate Precursor

A 500 ml four-neck flask with precision glass stirrer and internal thermometer and with a reflux condenser on top is initially charged with 105.4 g of an α,ω-dichloropolydimethylsiloxane of mean chain length N=5.5 together with 28.2 g of decamethylcyclopentasiloxane while stirring, and 5.6 g of concentrated sulfuric acid are added. The mixture is left to reactor at 50° C. for one hour and then at 100° C. for 2 hours. After cooling to 20° C., a colorless clear liquid is obtained.

b) Equilibration of the Precursor Having D/T Cycles Obtained in a)

110.8 g of a D/T siloxane prepared in analogy to Example 2 with a D/T ratio determined by $^{29}$Si NMR spectroscopy of 5.63:1 are added to the precursor obtained in a) while stirring within 5 minutes.

The equilibration is effected with vigorous stirring of the reactants at 22° C. for 30 minutes, then at 50° C. for 1 hour and at 100° C. for 6 hours.

With application of an auxiliary vacuum of 1 mbar, volatile constituents are removed at 50° C. over a period of 2 hours. After the liquid phase has been cooled, a water-clear colorless liquid having an acid value of 1.82 mmol of acid/g of substance (theoretically: 1.853 mmol of acid/g of substance) is isolated. $^{29}$Si NMR spectroscopy confirms the desired structure.

The invention claimed is:

1. A process for preparing a mixture of cyclic branched siloxanes having exclusively D and T units and having no functional groups, wherein the cumulative proportion of the D and T units having Si-alkoxy and/or SiOH groups that are present in the siloxane matrix; determinable by $^{29}$Si NMR spectroscopy, is ≤2 mole percent, wherein the ratio of the D and T units is between 10:1 and 3:1, and wherein a trialkoxysilane in a solvent is reacted with siloxane cycles or α,ω-dihydroxypolydimethylsiloxane with addition of water and in the presence of at least one acidic catalyst wherein the solvent is selected from the group consisting of toluene, cyclohexane, and ethyl carbonate in mass ratio of solvent to the siloxane of from 1:1 to 5:1, and wherein the process comprises a preliminary equilibration step at temperatures of T >40° C., followed by a condensation initiated by addition of water at temperatures of T >60° C.

2. The process according to claim 1, wherein the solvent is cyclohexane.

3. The process according to claim 1, wherein the acidic catalyst used is
   (a) selected from the group consisting of para-toluenesulfonic acid, trifluoromethanesulfonic acid, trichloroacetic acid, sulfuric acid, perchloric acid, phosphoric acid and hexafluorophosphoric acid, in amounts of from 0.1 to 2.0 percent by weight, based in each case on the silicon-containing component of the reaction matrix,
   or
   (b) a macrocrosslinked ion exchange resin containing sulfonic acid groups, in amounts of from 1.0 to 10.0 percent by weight, based in each case on the silicon-containing component of the reaction matrix.

4. The process according to claim 3, wherein the acidic catalyst used is
   (a) selected from the group consisting of para-toluenesulfonic acid, trifluoromethanesulfonic acid, trichloroacetic acid, sulfuric acid, perchloric acid, phosphoric acid and hexafluorophosphoric acid, in amounts of from 0.15 to 1.0 percent by weight.

5. The process according to claim 1, wherein the reaction is conducted at temperatures in the range from 10° C. to 150° C. and wherein the ratio of the D and T units is between 6:1 and 4:1.

6. The process according to claim 1, wherein the reaction is conducted at temperatures in the range from 40° C. to 110° C.

7. The process for preparing a mixture of cyclic branched siloxanes having exclusively D and T units and having no functional groups, wherein the ratio of the D and T units is between 10:1 and 3:1, and wherein the cumulative proportion of the D and T units having Si-alkoxy and/or SiOH groups that are present in the siloxane matrix determinable by $^{29}$Si NMR spectroscopy, is ≤2 mole percent, and wherein a trialkoxysilane in a solvent is reacted with siloxane cycles or α,ω-dihydroxypolydimethylsiloxane with addition of water and in the presence of at least one acidic catalyst.

8. The process according to claim 7, wherein the reaction comprises a preliminary equilibration step at temperatures of T >40° C., followed by a condensation initiated by addition of water at temperatures of T >60° C., where the water is added in one portion, in several portions or continuously.

9. The process for preparing branched organomodified siloxanes, wherein
   in a first step mixtures of cyclic branched siloxanes are provided, according to claim 7,
   and
   in a second step the mixtures of cyclic branched siloxanes are equilibrated under acidic conditions with silanes and siloxanes.

10. The process according to claim 9, wherein the silanes and siloxanes used are any acid-equilibratable silicon compounds, the silanes are selected from the group consisting of diethoxydimethylsilane, methyltriethoxysilane, trimethylalkoxysilane, and dimethyldichlorosilane, and the siloxanes selected from the group consisting of tetramethyldisiloxane, decamethylcyclopentasiloxane, α,ω-dihydropolydimethylsiloxanes, poly(methylhydro)siloxanes, α,ω-dialkoxypolydimethylsiloxanes or α,ω-divinylpolydimethylsiloxanes.

11. The process for preparing branched silicone oils, wherein in a first step mixtures of cyclic branched siloxanes are provided, according to claim 7, and in a second step the cyclic branched siloxanes are reacted with polydimethylsiloxanes or hexamethyldisiloxane.

* * * * *